United States Patent [19]

Hufnagle

[11] Patent Number: 4,994,068

[45] Date of Patent: * Feb. 19, 1991

[54] COMBINATION STERILE PAD SUPPORT AND LANCET CONTAINING LANCET DISPOSAL ELEMENT

[75] Inventor: Douglas R. Hufnagle, Columbus, Ohio

[73] Assignee: Unidex, Inc., Columbus, Ohio

[ * ] Notice: The portion of the term of this patent subsequent to Jan. 13, 2004 has been disclaimed.

[21] Appl. No.: 440,945

[22] Filed: Nov. 24, 1989

[51] Int. Cl.⁵ ............................................... A61B 17/34
[52] U.S. Cl. ..................................................... 606/181
[58] Field of Search ....................... 606/181; 128/770; 604/192

[56] References Cited

U.S. PATENT DOCUMENTS

| | | | |
|---|---|---|---|
| 2,117,469 | 5/1938 | Woodyatt | 128/215 |
| 2,627,269 | 2/1953 | McGregor | 128/215 |
| 2,642,065 | 6/1953 | Negri | 128/269 |
| 2,851,036 | 9/1958 | Lipari | 128/218 |
| 3,221,739 | 12/1965 | Rosenthal | 128/253 |
| 3,358,689 | 12/1967 | Higgins | 128/329 |
| 3,680,559 | 8/1972 | Gorbahn | 128/220 |
| 4,243,035 | 1/1981 | Barrett | 128/215 |
| 4,375,815 | 3/1983 | Burns | 128/314 |
| 4,635,633 | 1/1987 | Hufnagle | 128/314 |
| 4,712,548 | 12/1987 | Enstrom | 606/181 |
| 4,915,697 | 4/1990 | DuPont | 604/192 |

Primary Examiner—Max Hindenburg
Attorney, Agent, or Firm—John L. Gray

[57] ABSTRACT

This invention is directed to a cheap, disposable combination sterile pad support and lancet which may be used in connection with drawing blood for various tests including stat glucose levels for diabetics cholesterol determinations and others. It includes means for reinserting the lancet in the support following usage so that no individual will come in contact with the pointed end of the lancet. The sterile pad may be used to disinfect the end of the finger and then the lancet may be used to stick the finger to draw blood and the sterile pad may also be used on the stick site firmly thus aiding the blood clotting time after the drop of blood has been removed.

6 Claims, 2 Drawing Sheets

COMBINATION STERILE PAD SUPPORT AND LANCET CONTAINING LANCET DISPOSAL ELEMENT

BACKGROUND OF THE INVENTION

This is an improvement on my invention entitled "Combination Sterile Pad Support and Lancet", U.S. Pat. No. 4,635,633, which issued on Jan. 13, 1987.

Finger-stick blood sampling is practiced for a variety of purposes including use by diabetics who must test themselves for stat glucose levels up to four times a day in order to determine whether or not they should self-administer insulin, as well as for many different types of diagnostic tests which are conducted in physicians' offices or in hospitals, as well as finger-stick cholesterol blood screenings at such places as shopping malls, drug and grocery stores.

Applicant's invention as set forth in U.S. Pat. No. 4,635,633 is ideally suited for this purpose since the antiseptic pad and the lancet are contained in a single cheap disposable combination unit with the pad being used to disinfect the end of the finger and the lancet being used to stick the finger to draw blood. The pad may also be held on the stick site firmly thus aiding the blood clotting time after the drop of blood has been removed.

Today, because of various high-risk, life-threatening diseases that are prevalent throughout the world, extreme caution must be taken to protect the end user as well as others who may come in contact with disposable lancet needles.

At the present time there are two methods used in disposing of lancets of the type shown in U.S. Pat. No. 4,635,633. The first method is to use the round protective cap which was originally removed from the lancet and had been molded as part of the original lancet and attempt to insert the contaminated needle back into this plastic piece. This is very difficult to do because the round plastic part is small, the hole in it is even smaller, and the needle can slip away into the person who is attempting to accomplish this, who might very well be someone other than the person into whose finger the needle had been inserted. The other method in use is to discard the contaminated needle after use in some large container or trash receptacle with no protective cover on the needle. This is extremely dangerous because if the primary user does not immediately discard the lancet it becomes exposed to others who may not know of its status. Even if the lancet is disposed of in a general purpose trash container it exposes potential nonusers to the lancet sharp end with the attendant risks associated therewith if the lancet sharp end had been inserted into someone having a contagious life-threatening disease.

Furthermore, there is legislation pending in some jurisdictions to require that the lancet point be fully protected upon disposal in the case of certain institutional uses.

SUMMARY OF THE INVENTION

This invention is directed to a cheap, disposable combination sterile pad support and lancet which may be used to disinfect the end of the finger area and then used to stick the finger to draw blood and the pad may also be held on the stick site firmly thus aiding the blood clotting time after the drop of blood has been removed. After the lancet has been used it can be inverted and reinserted into the cylinder in which it had been originally held, which cylinder is provided with means in the interior thereof to grip the lancet and hold it in place and seal the used needle from exposure to anyone else.

Furthermore, the length of the lancet and the positioning of the lancet in respect to the cylinder which had held it can be such that there will no portion of the lancet extending beyond the cylinder end upon reinsertion therein so as to prevent anyone from removing it.

It is therefore an object of this invention to provide a small compact sterile pad support in combination with a protected sterile lancet.

It is an additional object of this invention to provide a device wherein the lancet when used may be reinserted into a support base and firmly held therein.

It is another object of this invention to provide such a device in which the lancet cannot be easily removed upon reinsertion.

These, together with other objects and advantages of the invention will become more readily apparent to those skilled in the art when the following general statements and descriptions are read in the light of the appended drawings.

DETAILED DESCRIPTION OF THE INVENTION

Figure 1:
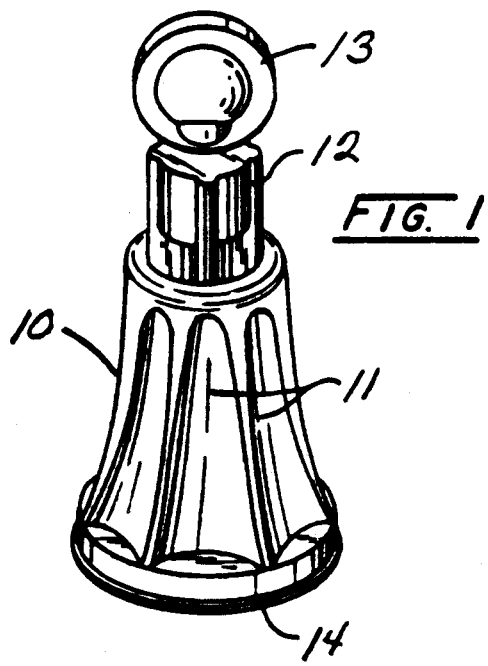
FIG. 1 is a perspective view of the combination sterile pad support and lancet.

Referring now more particularly to FIG. 1, the support member 10 is shown provided with a plurality of depressed finger engaging portions 11—11 providing a good grip for the user. Inserted in support member 10 and frictionally held therein is a lancet 12 such as that shown in U.S. Pat. No. 3,358,689, Higgins. Lancet 12 is provided with a protective cover 13 and a heat sealable foil 14 covers the base of the support member 10 thus preventing the antiseptic and the antiseptic impregnated absorbent pad in support member 10 from evaporating.

Figure 2:
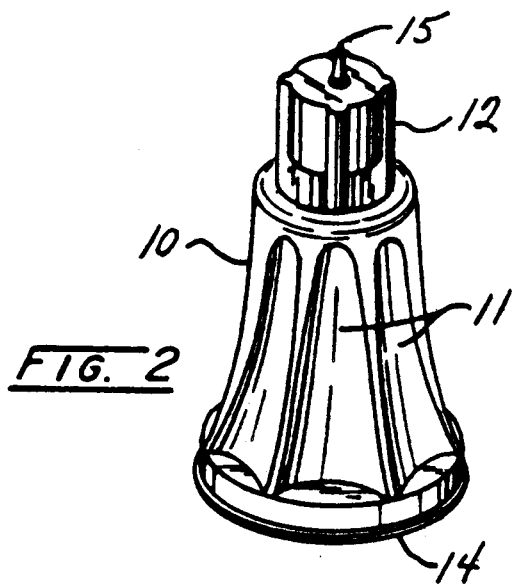
FIG. 2 is the same perspective view with the cover on the lancet removed.

Referring now more particularly to FIG. 2, the protective cover 13 has been removed revealing the pointed end 15 of the lancet 12.

Figure 3:
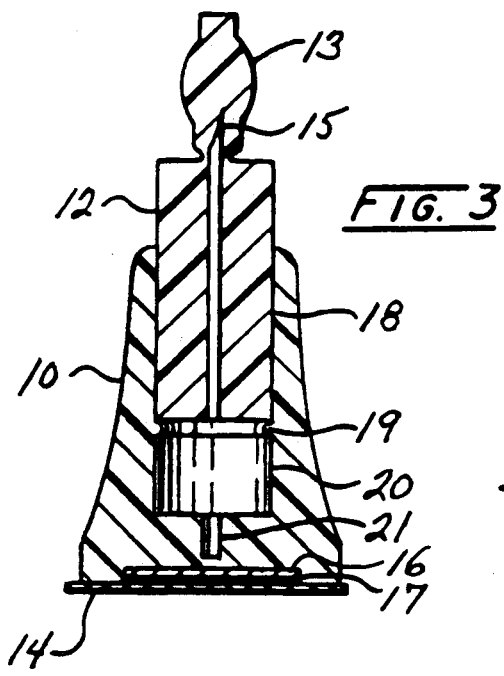
FIG. 3 is a sectional view of the combination sterile pad support and lancet shown in FIG. 1.

Referring now more particular to FIG. 3, the antiseptic impregnated absorbent pad 16 is shown held in place by the reverse bevel portion 17 of the recessed portion of support member 10 but other mechanical or adhesive fasteners can also be used. The pad 16 is of a size so that it will adequately clean and fit the end of a person's finger. The heat sealable foil 14 is heat sealed to the base of support member 10 around the periphery of the base thus preventing the antiseptic in pad 16 from evaporating and may be readily removed by peeling it off when the user is ready to prepare the site of the finger stick. The support member 10 is preferably made from injected low density polystyrene.

The lancet 12 is supported in cylinder 18 by means of an annular ring 19 which may be made as an integral portion of the support member 10 leaving a lower unused open portion 20 of the cylinder 18, the end of which is provided with a centrally positioned depression 21 of a size adapted to receive the pointed end 15 of the lancet 12 after use.

Figure 4:
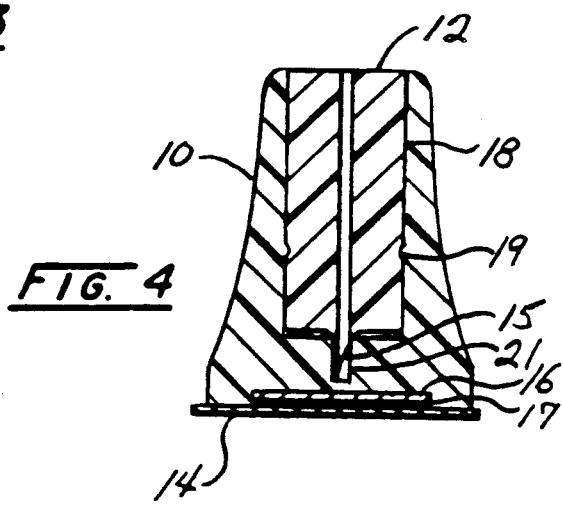
FIG. 4 is a sectional view of the combination sterile pad support and lancet with the lancet in inverted position after having been used.

Referring now more particularly to FIG. 4, the support member 10 is shown with the lancet 12 reinserted therein following usage. It will be noted that the ring 19 is of such a size that the lancet 12 will deform as it is passed over it and thus will be gripped and sealed in place in the cylinder 18 with the pointed end 15 of the lancet 12 sealed from exposure to anyone else. Preferably the lancet 12 is of a length so that when it has been reinserted into the cylinder 18 with the pointed end 15 in the depression 21, the end of the lancet 12 opposite to the pointed end will be flush with the top of support member 10 thus making it virtually impossible for the lancet 12 to be removed from the support member 10, and ensuring that no one else will come in contact with the used lancet's pointed end 15.

Figure 5:
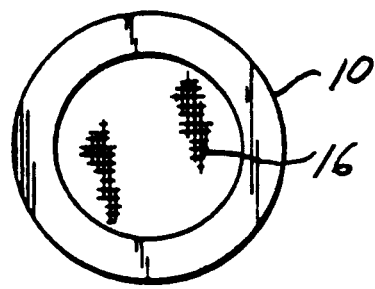
FIG. 5 is an end view of FIG. 3 with the protective cover on the sterile pad removed.

Referring now more particularly to FIG. 5, the end view of support member 10 is shown with foil 14 removed exposing the antiseptic impregnated absorbent pad 16. The pad 16 is of a size so that it will adequately clean and fit the end of a person's finger.

Figure 6:
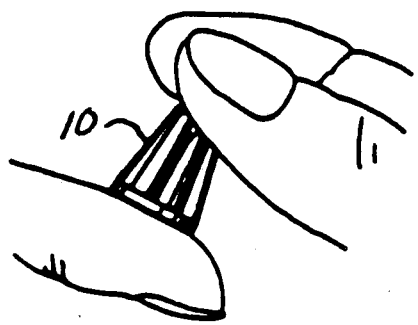
FIG. 6 shows the use of the device in preparing the site for the stick procedure and also showing the use of the device after the blood has been removed to aid in blood clotting.
Figure 7:
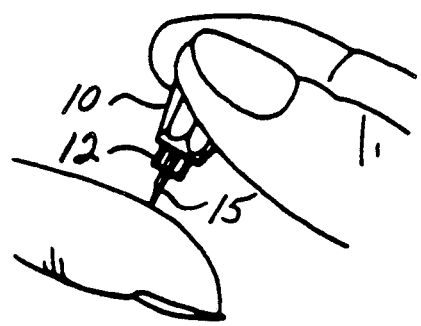
FIG. 7 shows the lancet being inserted in the stick site on an individual's finger.

Referring now more particularly to FIG. 6, the combination sterile pad and lancet is shown with the foil cover removed and with the antiseptic impregnated pad 16 in contact with the finger end thus disinfecting the area which will receive the lancet. The protective cover 13 is then twisted off and discarded leaving the sharp pointed end 15 of the lancet 12 exposed and the position of the device is reversed as shown in FIG. 7 so that the sharp pointed end 15 of the lancet 12 may be inserted in the finger or the lancet 12 may be removed from the support member 10 and used in conjunction with a mechanical device to puncture the skin. After the drop of blood has been removed the support member 10 may be placed with the pad 16 in firm contact with the stick site as in FIG. 6, thus aiding the blood clotting time. Preferably, before doing this the lancet 12 may be inserted into the cylinder 18 of support member 10 and pushed therein so that it achieves the position shown in FIG. 4 thus ensuring that the lancet tip will not come in contact with anyone else.

While this invention has been described in its preferred embodiment, it is to be appreciated that variations therefrom may be made without departing from the true scope and spirit of the invention.

What is claimed:

1. A combination sterile pad support and lancet comprising:
   a member provided with a base and containing a hollow cylinder, one end of said cylinder being closed and terminating adjacent to said base, the opposite end of said cylinder being open and terminating in the end of said member opposite to said base,
   a lancet, said cylinder being of a size and shape adapted frictionally to hold said lancet, said lancet being positioned in said cylinder,
   said lancet having a sharp pointed end on one end thereof and a removable cover on said sharp pointed end,
   said one end of said lancet extending out of said cylinder a distance so that said lancet may be readily pulled out of said cylinder,
   said hollow cylinder containing means for gripping said lancet when said lancet is reinserted into said cylinder with said sharp pointed end extending into said cylinder, after said cover on said sharp pointed end has been removed,
   said member being provided with a recess in the base of said member,
   an absorbent pad in said recess containing an antiseptic fluid,
   a removable cover on said base completely covering said pad and adapted to cooperate with said recess to prevent said antiseptic fluid from coming in contact with the atmosphere, said cover being separable from said pad whereby said pad will remain in said recess when said cover is removed from said base.

2. The combination sterile pad support and lancet of claim 1 wherein said member is in the shape of the frustum of a cone with the base of the cone being coextensive with the base of the member.

3. The combination sterile pad support and lancet of claim 2 wherein said conically-shaped member is provided with indented finger engaging portions on its outer surface.

4. The combination sterile pad support and lancet of claim 1 wherein said means for gripping said lancet when said lancet is reinserted into said cylinder consists of an annular ring extending into the interior of said cylinder.

5. The combination sterile pad support and lancet of claim 1 wherein said cylinder is provided at its closed end with a recess of a size adapted to receive the sharp pointed end of said lancet when said lancet is reinserted into said cylinder.

6. The combination sterile pad support and lancet of claim 5 comprising a lancet of a length so that when it is reinserted into said cylinder with said sharp pointed end of said lancet extending into said cylinder, the end of said lancet opposite the pointed end will be flush with the end of said member opposite said base.

* * * * *